(12) United States Patent
Carroll et al.

(10) Patent No.: US 7,693,322 B2
(45) Date of Patent: Apr. 6, 2010

(54) FOAM ASSESSMENT

(75) Inventors: John Carroll, Stockton-On-Tees (GB); Pamela Yvonne Shadforth, Billingham (GB); William Neville Eugen Meredith, Thirsk (GB)

(73) Assignee: Imperial Chemical Industries PLC, London (GB)

( * ) Notice: Subject to any disclaimer, the term of this patent is extended or adjusted under 35 U.S.C. 154(b) by 986 days.

(21) Appl. No.: 10/547,281

(22) PCT Filed: Feb. 24, 2004

(86) PCT No.: PCT/GB2004/000711
§ 371 (c)(1),
(2), (4) Date: May 25, 2006

(87) PCT Pub. No.: WO2004/077008
PCT Pub. Date: Sep. 10, 2004

(65) Prior Publication Data
US 2006/0210139 A1    Sep. 21, 2006

(30) Foreign Application Priority Data
Feb. 28, 2003   (GB) ................................ 0304719.8

(51) Int. Cl.
*G06K 9/00* (2006.01)
*G03G 13/10* (2006.01)
*G03C 8/00* (2006.01)

(52) U.S. Cl. ................. 382/141; 382/100; 430/117.31; 430/200

(58) Field of Classification Search ................. 382/141, 382/100; 430/117.31, 117.1, 200, 331, 306, 430/944, 964, 309; 399/249, 176, 330, 279, 399/357, 343, 331, 239, 333, 285, 284; 428/195.1; 492/56, 53, 59; 101/401.1; 219/216; 432/60; 439/491; 118/60, 260
See application file for complete search history.

(56) References Cited

U.S. PATENT DOCUMENTS 4,830,192 A     5/1989  Plester et al.
5,337,597 A  *  8/1994  Peake et al. .................. 73/45.5

(Continued)

FOREIGN PATENT DOCUMENTS

DE   3712377   10/1988
EP   0418005    3/1991

(Continued)

*Primary Examiner*—Sheela C Chawan
(74) *Attorney, Agent, or Firm*—Jones Day

(57) ABSTRACT

There are described methods and apparatus for assessing foams generated from liquids. Existing methods are slow and labor intensive. The new methods involve generating foams from liquids and optically obtaining information to enable parameters relating to the generated foam to be measured. Although single samples of liquids may be processed the methods are particularly suited to processing multiple samples to obtain data relating to foams at a high rate. The apparatus includes automated handling equipment to enable samples to be moved between workstations and relative to associated optical equipment that is used to obtain information relating to the foams.

19 Claims, 9 Drawing Sheets

U.S. PATENT DOCUMENTS

| | | | |
|---|---|---|---|
| 5,465,610 A * | 11/1995 | Loisel | 73/60.11 |
| 5,566,249 A | 10/1996 | Rosenlof et al. | |
| 5,597,950 A * | 1/1997 | Mullen | 73/60.11 |
| 6,977,723 B2 * | 12/2005 | Lemmo et al. | 356/301 |

FOREIGN PATENT DOCUMENTS

| | | |
|---|---|---|
| EP | 0544428 | 6/1993 |
| EP | 0655610 | 5/1995 |
| EP | 0753730 | 1/1997 |
| WO | 03009233 | 1/2003 |

* cited by examiner

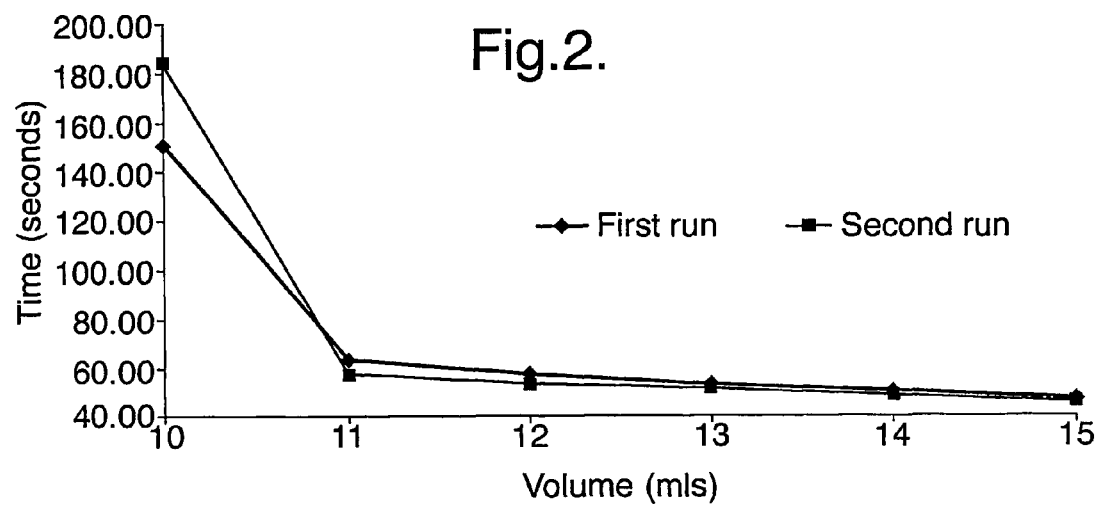
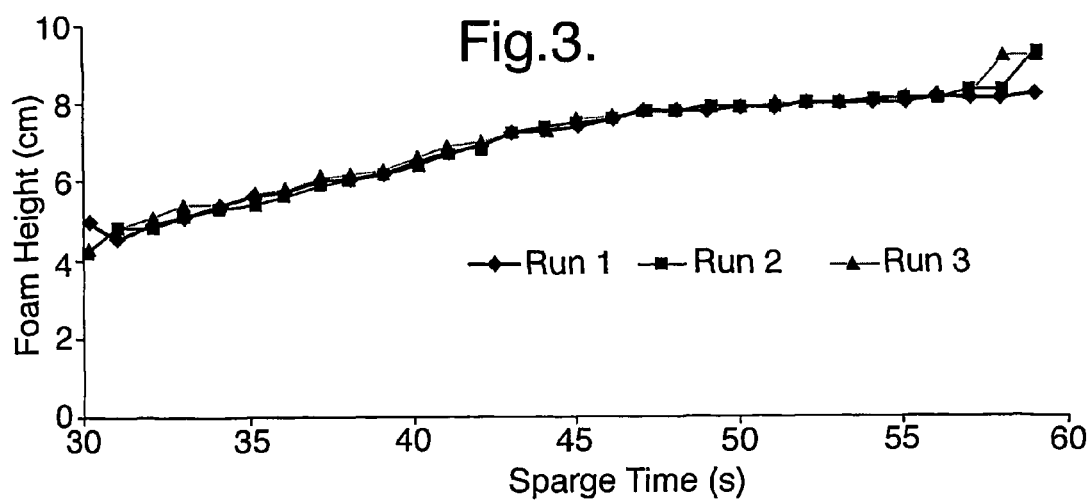

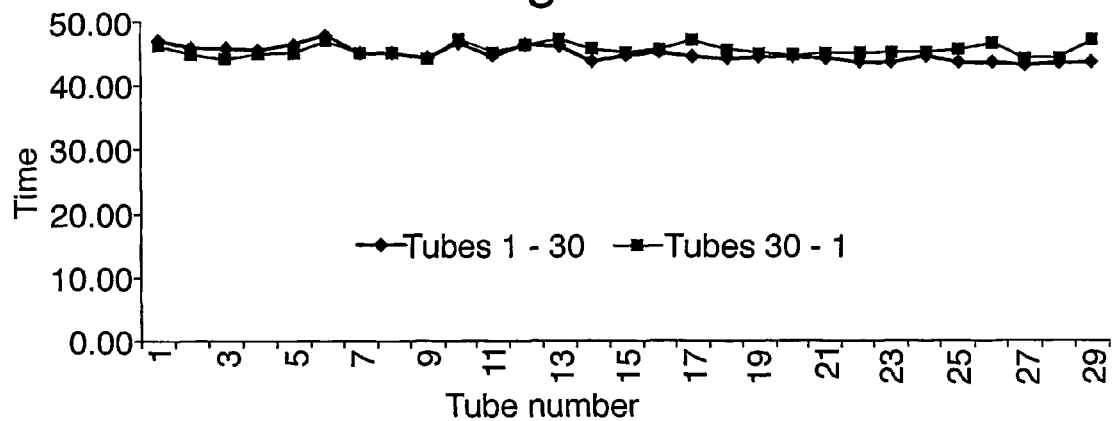
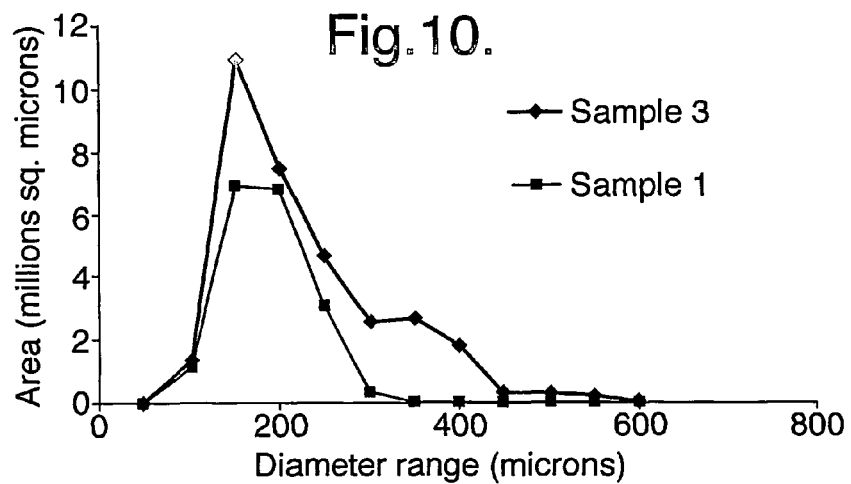

FOAM ASSESSMENT

CROSS REFERENCE TO RELATED APPLICATION

This application is the National Phase application of International Application No. PCT/GB2004/000711, filed Feb. 24, 2004, which designates the United States and was published in English. This application, in its entirety, is incorporated herein by reference.

The invention relates to the measurement and assessment of foams.

Foam generation from liquids is a phenomenon that attracts significant attention. For example, the generation of good quality foam, as perceived by users, from personal care products such as shampoos and other cleansing formulations may add significantly to the commercial value of such products. Beverages, eg beers, cola drinks, cappuccino coffee, is another consumer-oriented area in which foams, possibly transient foams, are important in the perception of quality. In other areas such as lubricants and engineering fluids, foams may be detrimental to the performance of such fluids; alternatively, for some applications, it may be advantageous to generate foams in such fluids.

In some applications, it may be sufficient to discriminate between liquids that generate foams by categorising them as high, medium or low foam-generating liquids. Such an assessment can be achieved for lubricants by using ASTM D892-95, which method measures foam height at predetermined intervals and temperatures. Whilst providing good discrimination between foams, this method is labour intensive, relatively slow and costly to carry out.

The effect of surfactants in base liquids may also be assessed using ASTM D 1173-53 (Re-approved 1997). However, again this method is labour intensive, relatively slow and costly to carry out.

The quality of foams may also be determined at least in part by the size and density of bubbles forming the foam. Smaller, more dense, ie greater number, bubbles tend to mean the foam has greater stability, ie persistence, and, in shampoos etc, better feel and similar customer-oriented properties. Conversely, large, less dense, bubbles tend to be more transient which again, in customer-oriented product areas, may be part of the commercial value of the products.

In the personal care area, expert panels do such assessments subjectively. Such panels consist of people trained to generate foams and make an assessment of parameters such as foam "whiteness" (assessment of bubble size), bubble size distribution, prevalence of large bubbles etc. Clearly, such methods are labour intensive, slow and costly and do not necessarily provide consistent results.

There is, however, a significant problem in assessing the foaming capability of formulations, whether containing foam-generating materials such as surfactants or foam-suppressing materials such as silicon-based materials, on a consistent basis.

Owing to commercial pressures to produce better, more cost-effective formulations, high throughput screening (HTS) is being developed from its origins in pharmaceutical and biotechnology applications to everyday products to enable the screening of large numbers of materials to generate data banks from which new products can be identified and generated. Clearly, the methods described above are not suitable for relatively high speed screening of large numbers of formulations using HTS techniques.

Some attempts have been made to give a more quantitative analysis of foams: A Fains et. al., "Stability and Texture of Protein Foams: A Study by Video Image Analysis" Food Hydrocolloids 11(1) 63-69 (1997); H H Fiori et. al. "Computerised Image Analysis of Bubbles in Gastric Aspirate for Prediction of Respiratory Distress Syndrome" Acta Paediatr. 90, 1402-1404 (2001); R Sanchez-Vioque et. al. "Foaming Properties of Acylated Rapeseed Hydrolysates" J. Colloid Interface Sci. 244, 386-393 (2001); and N J Hepworth, J Varley & A Hind "Characterising Gas Bubble Dispersions in Beer", Inst. Chem. Engineers Trans. IchemE 79, 13-2-(March 2001). However, the techniques described in those references again do not enable the relatively high speed screening of large numbers of formulations.

It is an object of the present invention to provide a method of assessing foam that is consistent across samples and is reasonably fast.

It is another object of the present invention to provide a method of assessing foam that is consistent across samples and is reasonably fast and is capable of being adapted as a high throughput screen to assess foams.

According to a first aspect of the present invention, a method of assessing foam generation from a liquid comprises:

a) introducing a measured quantity of the liquid into a tube;

b) after a predetermined period, generating a gas flow of predetermined flow rate into said liquid to generate a foam from the liquid in the tube;

c) using an opto-electronic device that is capable of generating data relating to foam in the tube to obtain data relating to the foam generated in the tube; and d) using the data to assess the foaming ability of the liquid.

In one form of the method according to the first aspect of the invention, the gas is passed through the liquid for a predetermined period unless data from the opto-electronic device indicates the presence of the top of the foam being generated before said period expires. This enables a simple high foaming/not high foaming assessment to be made of liquids under test based on whether the top of the foam being generated is detected in less than the predetermined gas flow period. Provided liquids generate sufficient foam to be detected by the opto-electronic device in less than the predetermined period, some differentiation of liquid foaming ability of the liquids may be possible based on time taken to foam detection.

In an alternative form of the method according to the first aspect of the invention, the height of the foam generated is detected to enable a quantitative assessment to be made of the foaming ability of the liquid. In this form of the method, the gas is passed through the liquid for a predetermined period unless data from the opto-electronic device indicates the presence of the top of the foam being generated before said period expires. If data from the opto-electronic device indicates the presence of the top of the foam being generated before the expiry of the predetermined period, the foam is classed as having high foaming ability; if data is not generated by the device, ie the top of the foam is not detected, before said period expires, on expiry of said period the gas flow is stopped and relative movement of the tube and the opto-electronic device with respect to one another enables the height of the foam generated in said period to be measured. Preferably, the opto-electronic device is moved relative to the tube. Preferably, the optoelectronic device generates data relating to the positions of the air/foam and the foam liquid interfaces, the difference between the positions being the height of the foam generated from the liquid in said period.

Thus, liquids can be assessed as to whether they have a high foaming ability or qualitatively have a foaming ability less than high, eg medium or low, depending on the height of foam measured.

Thus, the method according to the first aspect of the invention enables a rapid and simple assessment of the ability of a liquid to generate foam and to screen high numbers of such liquids for that ability.

Clearly, as discussed earlier, it would be advantageous to assess liquids not only on their ability to generate foam but also on the quality of the foam produced. This may be particularly important when seeking to differentiate between a number of liquids that have similar foam-generation ability.

According to a second aspect of the present invention, a method of assessing the quality generated from a liquid comprises:

a) introducing a measured quantity of liquid into a tube;
b) after a first predetermined period, generating a gas of predetermined flow rate into the liquid to generate a foam from the liquid in the tube;
c) after a second predetermined period, stopping the gas flow and measuring the height of the foam generated in the tube;
d) in response to the height data generated in step c), positioning an opto-electrical device at a location externally of the tube by relative movement of the tube and the optoelectronic device with respect to one another, the device being capable of capturing an image of the foam;
e) capturing an image of the foam; and
f) analysing the captured image for parameters relevant to foam quality.

Preferably, the height of the foam generated in the tube is determined using a second optoelectronic device capable of generating data relating to foam in the tube. In one form of the method according to the second aspect of the invention, relative movement of the tube and the second opto-electronic device with respect to one another enables the height of the foam generated in said period to be determined. Preferably, the tube is moved relative to the second opto-electronic device. Preferably, the second opto-electronic device generates data relating to the positions of the air/foam and the foam/liquid interfaces, the difference between the positions being the height of the foam generated from the liquid in said period.

In a preferred form of the method according to the second aspect of the invention, the second opto-electronic device is fixed relative to the tube position and captures an image of the whole foam head that is analysed to provide a measurement of foam height.

The first opto-electrical device is positioned at a location externally of the tube by relative movement of the tube and the first opto-electronic device with respect to one another. In one form of the the method according to the second aspect of the invention, relative movement of the first opto-electronic device and the tube and with respect to one another is achieved by moving the first opto-electronic device relative to the tube.

Although the location externally of the tube at which the first opto-electrical device is positioned may be anywhere relative to the foam volume that may be of interest, a convenient location is approximately half the measured height of the foam. For many liquids, such a position is both remote from the liquid/foam interface, at which bubbles tend to be very uniform, and remote from the foam/air interface, at which the foam is too aged and is deteriorating.

In a preferred form of the method according to the second aspect of the invention, relative movement of the first opto-electronic device and the tube and with respect to one another is achieved by moving the tube relative to first opto-electronic device.

The image captured by the first opto-electronic device is subjected to analysis by suitable software, for example the KS300 Image Analysis System available from Carl Zeiss Vision GmbH, Hallbergmoos, Germany. The software is configured to analyse the image for information of interest.

Thus, according to a third aspect of the present invention, a method of analysing an image of foam generated from a liquid comprises subjecting a digital, black and white image (image 1) of the foam to the following operations:

a) subjecting image 1 to a watershed segmentation process to produce an image (image 2) in a graphics plane associated with the electronic frame, image 2 being a line representation of bubble walls of the foam;
b) clearing image 1 from the image plane of the frame and merging the graphics plane with the image plane of the frame to create a binary image (image 3) consisting of lines representing the bubble walls and a contrasting background and clearing image 2 from the graphics plane; and
c) measuring the dimensions of the bubbles in the image.

It will be appreciated that, in the binary image 3, the lines may be black or white and the contrasting background white or black, respectively. However, in a preferred embodiment, in step b), in image 3 the lines are white and the background, the bubble voids, is black. Preferably, before step c), image 3 is inverted to create an image 4 in which the bubble walls are black and the bubbles are white, image 4 being the image used in step c).

Image 1 may be obtained as a black and white image or as a colour image which is processed to be a black and white image. The colour image may be processed by selecting at least one information channel (red, green or blue) of the digital image and creating therefrom the black and white image 1 in an electronic frame.

The method according to the third aspect of the invention may include subsidiary steps to improve the quality of the images being processed. For example, if the lighting used during capture of the image of the foam results in a shading across the image, image 1 is subjected to a smoothing operation, eg using a lowpass filter, to create a smoothed image (image 1a) followed by a shade correction process using image 1a to produce an image (image 1b) corrected for shading differences. It is then image 1b that is subjected to the watershed segmentation process in step b) of the preceding paragraph.

Other processes include erode and open operations to clean up the boundaries of the bubbles and to improve the differentiation of the spacing between the bubbles, ie the bubble walls. It is also possible to reduce or eliminate errors resulting from images of bubbles visible through larger bubbles at the front of the image. That is achieved by subjecting image 1, or image 1b as the case may be, to an adaptive segmentation process to produce a binary image (image 5) (the adaptive segmentation is done "locally" in the image not globally). The purpose of this step is specifically to produce a binary image of the big bubbles alone to enable features arising from bubbles behind, in the image, the big bubbles to be minimised. This is achieved by setting the size parameter and the threshold parameter (the big bubbles tend to also be lighter) for the adaptive segmentation process before carrying it out. The image 5 essentially contains images of just the big bubbles (or the main parts of them). That image is then subjected to a scrap operation to remove small white features within the black areas and a fill operation to fill in holes in the white objects so they are more complete (image 6).

To further improve the quality of the data obtained, image 4 may be inverted so that it shows white lines and black blobs. Some of these white lines are incorrect since they are from subsurface bubbles. The inverted image 4 and image 6 are then subjected to a Boolean "SUBTRACT" operation to generate an enhanced image 4 on which, following an invert operation, and optionally other operations such as thin, prune, dilate and open operations, the measurements are made. The Boolean operation causes the white blobs of image 6 cancel out some of the lines of image 4 that are the result of subsurface bubbles.

According to a fourth aspect of the present invention, a method of determining the height of foam generated from a liquid in a tube comprises subjecting a digital black and white image of the foam in the tube to the following electronic operations:

a) copying the digital image (image 1) into an electronic frame (image 2) and then clearing image 2 from this frame to create a new blank frame having the same pixel dimensions as the original digital image 1;

b) creating a rectangle in a graphics plane associated with the electronic frame and merging the graphics plane with the image plane of image 2 and specifying the rectangle is white or black and the remainder is black or white, respectively, thereby creating a binary image (image 3) of a rectangle on a contrasting background, the rectangle having dimensions longer than the anticipated length of the foam being measured and narrower than the width of the internal dimension of the tube;

c) subjecting the original digital image 1 to a segment process to generate a binary image (image 4);

d) subjecting image 3, after an inversion operation if required, and image 4 to a Boolean "AND" operation to create an image (image 5) representative of the foam height; and e) measuring image 5 to determine the foam height.

Preferably, in step b), the rectangle is white and the remainder is black.

In the methods of the invention, it is preferred to use a gas diffuser means to generate gas flow through the liquid to generate foam therefrom. To obtain consistent results, it is necessary to "condition" the diffuser means by exposing it to the liquid under test for a predetermined period (as identified in step b) of the methods described above) before passing gas through the liquid. In many instances, exposure of the diffuser means to the liquid under test for the predetermined period in steps b) of the methods is sufficient to condition the diffuser means.

However, for some types of liquid, especially after the diffuser means has been allowed to stand dry for a period of time, it may be necessary to iterate the steps of the methods for a number of times on the same liquid until consistent results are obtained. When it is determined that iteration of the method is required to condition the diffuser means in this manner, the conditioning may be performed using a liquid that is similar to the liquid under test. Once conditioned, it is only necessary to clean the diffuser means between tests. Thus, once the diffuser means is conditioned, a multiplicity of tests can be performed without the need to re-condition the base by iteration of the methods, the conditioning of the diffuser means by the liquid under test that is achieved by steps b) of the methods being sufficient to enable consistent results to be obtained.

The gas flow rates and predetermined periods are selected to ensure the foam generated from any particular type of liquid under investigation does not completely fill the tube and overflow from it.

The methods of the invention also include the steps of cleaning the diffuser means and the tube between samples. The particular cleaning regime adopted may be dependent upon the liquids under investigation. Typically, however, such cleaning can be done after removal of the diffuser means from the liquid sample by placing the diffuser means into water (preferably de-ionised water) and flowing gas through the diffuser means; placing the diffuser means into a volatile liquid, for example acetone, and flowing gas through the diffuser means; and removing the diffuser means from the volatile liquid whilst continuing to flow gas through the diffuser means to evaporate the volatile liquid and dry the diffuser means. The cleaning process can be augmented with ultrasonic cleaning whilst the diffuser means is immersed in the water and the volatile liquid.

Using the methods of the invention, a typical sample time including subsequent cleaning of the diffuser means is under 10 minutes. Owing to the simplicity of the methods, a large number of samples can be tested using them. The samples may be tested singly and sequentially or, alternatively, and more preferably, batches of samples can be tested in parallel. Accordingly, the methods of the invention include processing batches of samples either sequentially or in parallel. When the samples are processed in parallel, preferably more than 1 sample but not more than 100 samples, more preferably at least 10 samples but not more than 50 samples are processed together.

It would be possible to provide sufficient opto-electronic devices to measure the foams generated substantially simultaneously. However, it is preferred to minimise the number of such devices used in the methods. Accordingly, it is preferred, in each batch of samples, to sequence the introduction of the diffuser means into the liquid samples and the associated gas flows and predetermined periods in successive tubes in the batch such that for example a single optoelectronic device or a single set of first and second opto-electronic devices, as the case may, is sequenced to each tube in the batch in turn to make the respective measurements and capture the images as foam is generated in that tube.

According to a fifth aspect of the present invention, apparatus for assessing foam generation from a liquid comprising a tube open at one end for receiving liquid samples and in which foams can be generated, a gas diffuser means locatable within the tube and through which a gas flow through a sample located within the tube can be generated, a gas flow control means whereby gas flow through said diffuser means is controllable, an opto-electronic device located in use adjacent the tube, said opto-electronic device being capable of generating data relating to foam in the tube, and control means for initiating action in response to input from the opto-electronic device.

The term tube as used herein means any conveniently shaped receptacle capable of holding a relatively small sample of liquid, of receiving a diffuser and of containing foam generated from the liquid. As it needs to be optically transparent, it is made from glass or other optically transparent material that is effectively chemically inert to the liquids under test. Conveniently, the tube is a test tube typically having a length in the 150 mm, and has an internal diameter of 25 mm.

The gas diffuser means is conveniently a gas diffuser in the form of a metal sinter having a plurality of holes passing through it. The metal sinter is secured to one end of a tube that is connectable to a gas supply. The holes in the metal sinter may have a diameter in the range 1-50 microns, more particularly in the range 2-20 microns, especially 2 microns. Suitable sinters are available from Fisher Scientific, Bishop Meadow Road, Loughborough, Leicestershire LE11 5RG. The gas supply tube typically has a length of 500 mm and has an internal diameter of 5 mm. The gas supply tube is connected to the gas supply via a flexible, gas impermeable tube.

A suitable flow controller controls gas flow through the diffuser means. Preferably, the controller is a mass flow controller, for example an Omega Mass Flow Controller available from Omega Engineering Ltd, 1 Omega Drive, River Bend Technology Centre, Northbank, Irlam, Manchester M44 5Ex. The gas supply associated with the apparatus according to the invention is typically a compressed air supply capable of supplying air at pressures up to 30 psi (2.07 bar).

According to one form of the fifth aspect of the present invention, the opto-electronic device is capable of detecting the top of foam being generated in the tube and, in response thereto, providing an output to the control means in response to which the control means is operable to terminate gas flow to the diffuser and to store the time taken from initiation of the gas flow to termination of the gas flow.

According to another form of the fifth aspect of the present invention, the opto-electronic device is capable of detecting the top of foam being generated in the tube and, in response thereto, providing an output to the control means in response to which the control means is operable to terminate gas flow to the diffuser and to store that event, the control means also being operable to control gas flow for a predetermined period unless it receives input from the opto-electronic device within said period and, if said period expires, terminating gas flow and initiating relative movement between the tube and the optoelectronic device whereby parameters that enable the height of the foam generated in said period are determinable.

Preferably, the opto-electronic device is moved relative to the tube. Preferably, the opto-electronic device detects the air/foam and the foam/liquid interfaces, the difference between the positions of said interfaces being the height of the foam generated from the liquid in said period.

In these forms of the fifth aspect of the present invention, the opto-electronic device is preferably a photoelectric device whose beam in use is interruptible by the foam but not by air or the liquid. A suitable device is a turbidity detector available from Zymark Corporation, Zymark Center, Hopkinton, Mass. 01748 USA.

According to yet another form of the fifth aspect of the present invention, the opto-electronic device is capable of capturing an image of the foam from a location externally of the tube, the control means being operable to initiate relative movement of the tube and the optoelectronic device with respect to one another to position the opto-electronic device at a location relative to the tube at which location, in use, the image is captured.

Preferably, apparatus according to the fifth aspect of the invention comprises a second opto-electronic device operable to generate data from which the height of foam generated in the tube may be determined.

In one form of the apparatus according to the fifth aspect of the invention, the tube and the second opto-electronic device are mounted for relative movement with respect to one another. Preferably, the tube is moved relative to the second opto-electronic device.

In one form of the apparatus according to the fifth aspect of the invention, the second optoelectronic device detects the air/foam and the foam/liquid interfaces and provides inputs into the control means from which the height of the foam generated is determinable. In this embodiment, the second opto-electronic device may be a photoelectric device as described previously.

In a preferred form of the apparatus according to the fifth aspect of the invention, the second opto-electronic device is fixed relative to the tube position and is capable of capturing an image of the whole foam column that, in use, is generated in the tube and transmitting such an image to the control means, the control means being operable to analyse the image so received to provide a measurement of foam height.

The opto-electronic devices capable of capturing images are conveniently charged couple device (CCD) cameras, having an analogue or digital output. As it merely needs to detect foam height, the second device is conveniently a low-resolution black and white camera, for example a camera having a pixel resolution of 752×582. For example, a Sony XC-75CE using a Pentax 25 mm f1.4 lens is a suitable camera. The first device, as it is required to capture an image of the constituent bubbles of the foam, is a medium- or high-resolution camera, for example a camera having a pixel resolution of 1300×1030. For example, an AxioCam MRC available from Carl Zeiss Vision GmbH is a suitable camera. Appropriate lens selection enables resolutions down to bubble sizes of 50 microns or less. A Computar 55 mm f2.8 Telecentric fens set at maximum zoom with a 35 mm extension tube is preferred.

Although it is possible to consider using a single camera, ie a single opto-electronic device, to capture images for both foam height measurement and for image analysis, owing to the opposed requirements of wide angle v narrow angle for each of the images, it is preferred to use two cameras, or two opto-electronic devices, as described above.

As will be well understood, suitable lighting has to be provided to enable the images to be captured. Conveniently, two light sources are used. To enable the second camera to capture an image of the whole foam column, front lighting (relative to the camera position) but at an offset position to avoid back reflection of the light to the camera is provided during image capture. A suitable light source is a cold cathode LP-100 lamp available from Universal Electronics Industries Ltd. For the first camera, the tube is lit from below to highlight the foam features and a suitable light source is a Schott cold light source with a gooseneck fibre optic cable.

It is preferred that extraneous light sources are excluded to avoid back reflections that may affect the quality of the captured image. Preferably, a surrounding non-reflective environment is provided to minimise further the possibility of extraneous reflections being captured as part of the images.

In preferred embodiments of the apparatus according to the fifth aspect of the invention, the apparatus further comprises a workstation at which is located the opto-electronic device or devices and automated handling equipment for moving the tube relative to said workstation and for positioning the gas diffuser means in the tube, said control means being adapted to control said automated handling equipment to move the tube to and from the workstation, to move the tube and the opto-electronic device or devices relative to one another and to move the gas diffuser means into and out of the tube.

Preferably, one or more tubes in which cleaning fluids for the gas diffuser means are locatable are provided at the workstation or at a separate, cleaning, workstation, said automated handling equipment being controllable by the control means to sequentially move the gas diffuser means between the first tube and the cleaning tube or tubes. An ultrasonic cleaner is preferably provided at this location. The tubes containing an appropriate cleaning fluid are located in an ultrasonic bath and are replaced after each cleaning cycle.

The present invention, in a sixth aspect, encompasses apparatus for assessing foam generation from a liquid comprising a workstation at which is located an opto-electronic device capable of generating data relating to foam generated from liquid located in a tube, a gas diffuser means locatable within a tube into which a liquid sample can be located and through which a gas flow into such a sample can be created, a gas flow control means whereby gas flow through said diffuser means is controllable, automated handling equipment for moving a tube relative to said workstation and for positioning the gas diffuser means in such a tube, and control means for initiating action in response to input from the opto-electronic device and being adapted to control said automated handling equipment to move a tube to and from the workstation and relative to the opto-electronic device whilst it is located at the workstation and to move the gas diffuser means into and out of a tube.

Automated sample handling is achieved using a Zymark XP trackless robot system, available from Zymark Corporation, Zymark Center, Hopkinton, Mass. 01748 USA, with a variety of associated workstations. Control of the system and the opto electronic device is carried out by means of Easylab robot control programming language.

As discussed in relation to the methods of the invention, although sample tubes may be fed sequentially through the foam-generation, measurement and cleaning cycle, samples may be processed in parallel. Thus, in another embodiment, the control means and the automated handling means are capable of moving the opto-electronic devices relative to the workstation passed a plurality of locations at which sample tubes are locatable. In this embodiment, preferably a plurality of diffuser means are provided each with it own cleaning station.

Associated with the or each workstation may be liquid supply means such as liquid injectors to enable samples to be introduced to the sample tubes, to provide fresh cleaning fluids to the cleaning stations and to provide automated waste disposal. Alternatively, racks of sample tubes may be prepared remotely from the workstation and the racks can then be introduced to a workstation accessible by the automated handling means. Following use, the sample tubes may then be disposed off, this being more economical than cleaning the sample tubes and re-using them. The tubes for the cleaning station can be managed in a similar manner.

A particularly preferred form of apparatus for assessing foam generation from a liquid comprises at least one first workstation at which is located, in use, sample tubes and cleaning tubes, a second workstation at which is located sample dispensing means, a third workstation at which, in use, cleaning tubes are locatable, a fourth workstation having a parking location for receiving a gas diffuser means that can be placed within a sample and through which gas flow can be generated and a gas flow control means whereby gas flow through said diffuser means is controllable, and a fifth workstation at which is located an opto-electronic device capable of generating data relating to foam generated from liquid located in a sample tube, said apparatus further comprising automated handling equipment and control means for initiating action in response to input from the opto-electronic device and being adapted to control said automated handling equipment, in use of the apparatus, to move cleaning tubes between the first and third workstations and to move sample tubes from the first workstation to the fourth workstation, to locate the gas diffuser means in the sample tube and to move the sample tube containing the gas diffuser means to the fifth workstation and to move the tube and the opto-electronic device relative to one another.

The invention also includes at least one library of data relating at least to the foam properties of liquids, said data having been generated using the methods and/or apparatus according to the invention.

The invention will now be illustrated by reference to the drawing and following examples. The drawings are:

FIG. 2 is a graph of time to generate a specified height of foam v volume of sample using Sample 3 as described in Example 1;

FIG. 3 is a graph of the results of foam heights achieved over time using Sample 3 as described in Example 1;

FIG. 4 is a graph of the results of foam heights achieved over time using a multiplicity of portions Sample 3 as described in Example 1 to demonstrate reproducibility;

Figure 5:
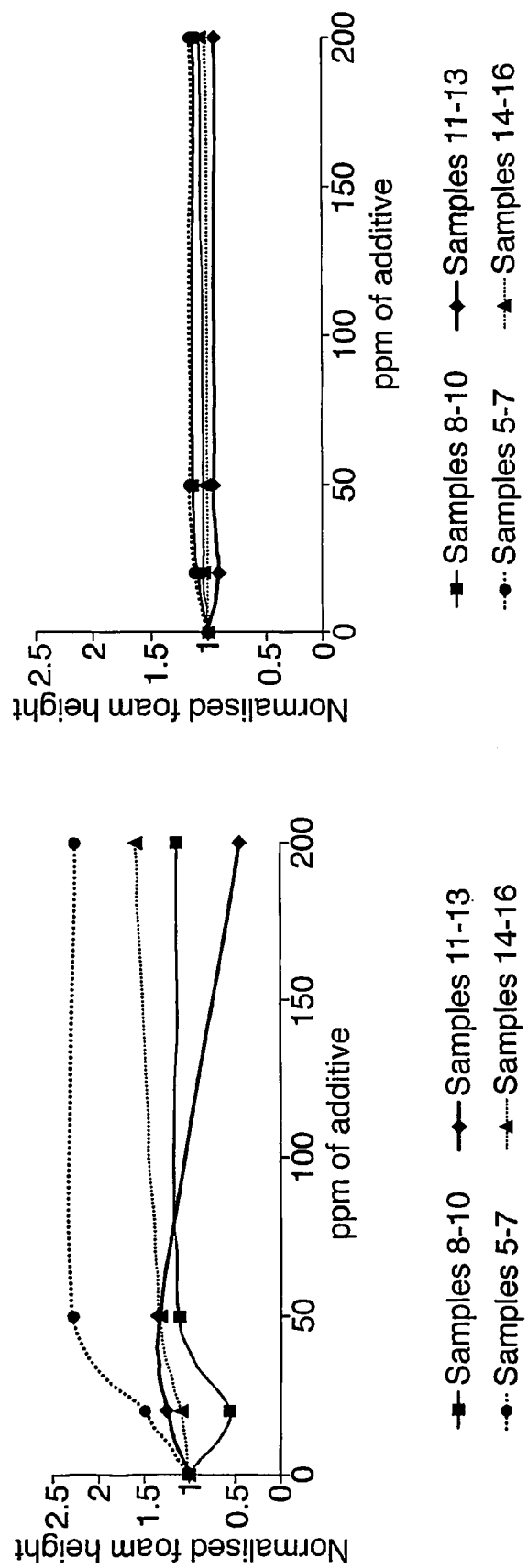
Figure 6:
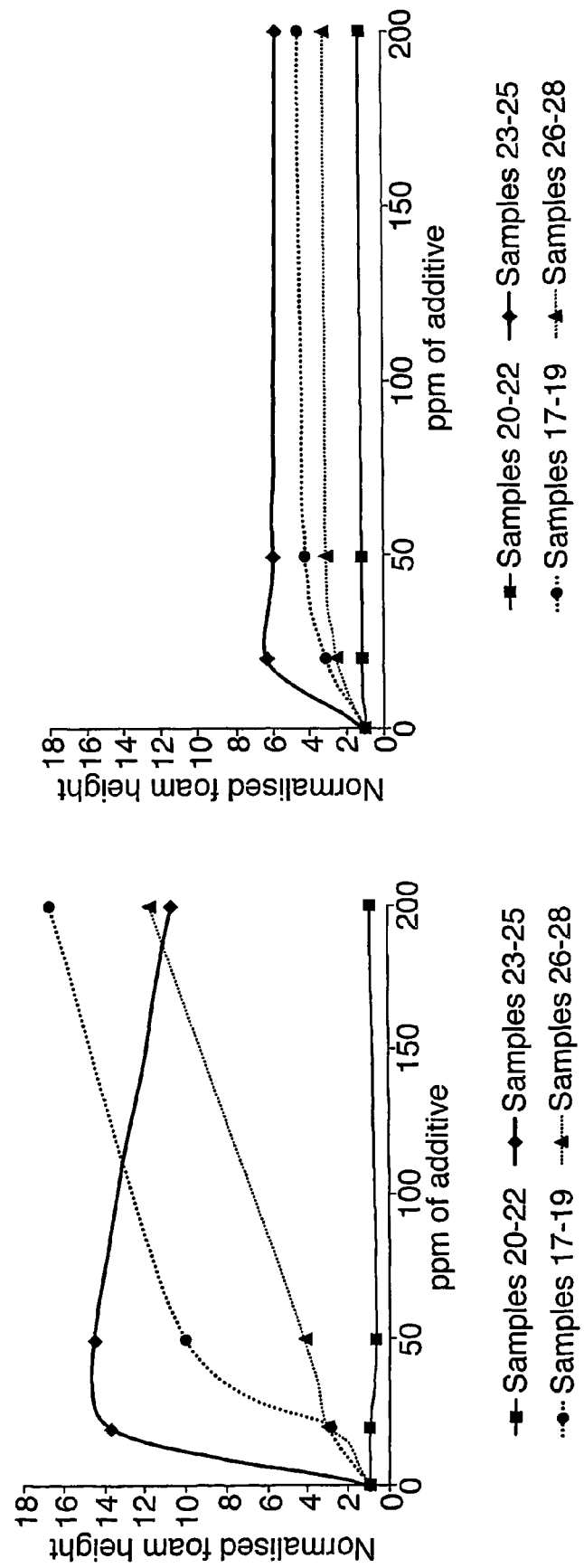
Figure 7:
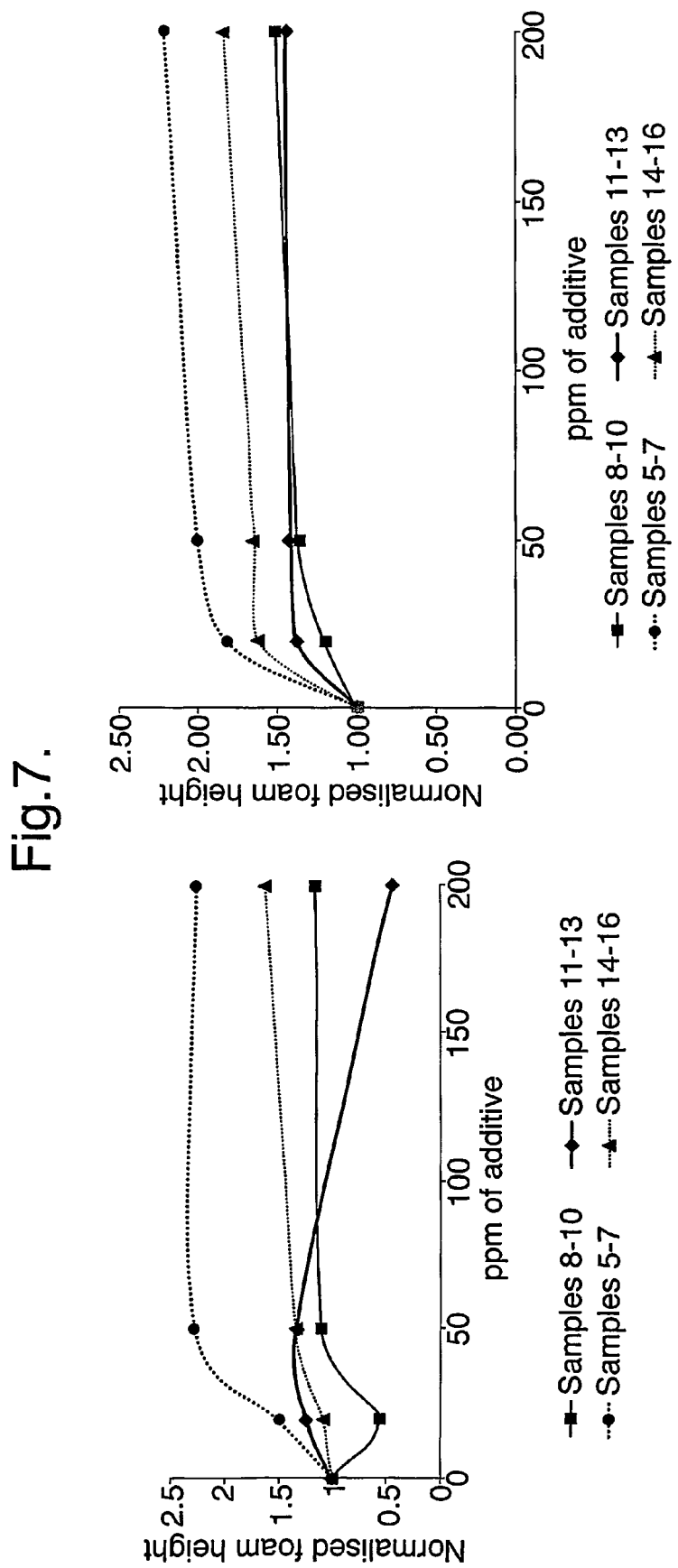
Figure 8:
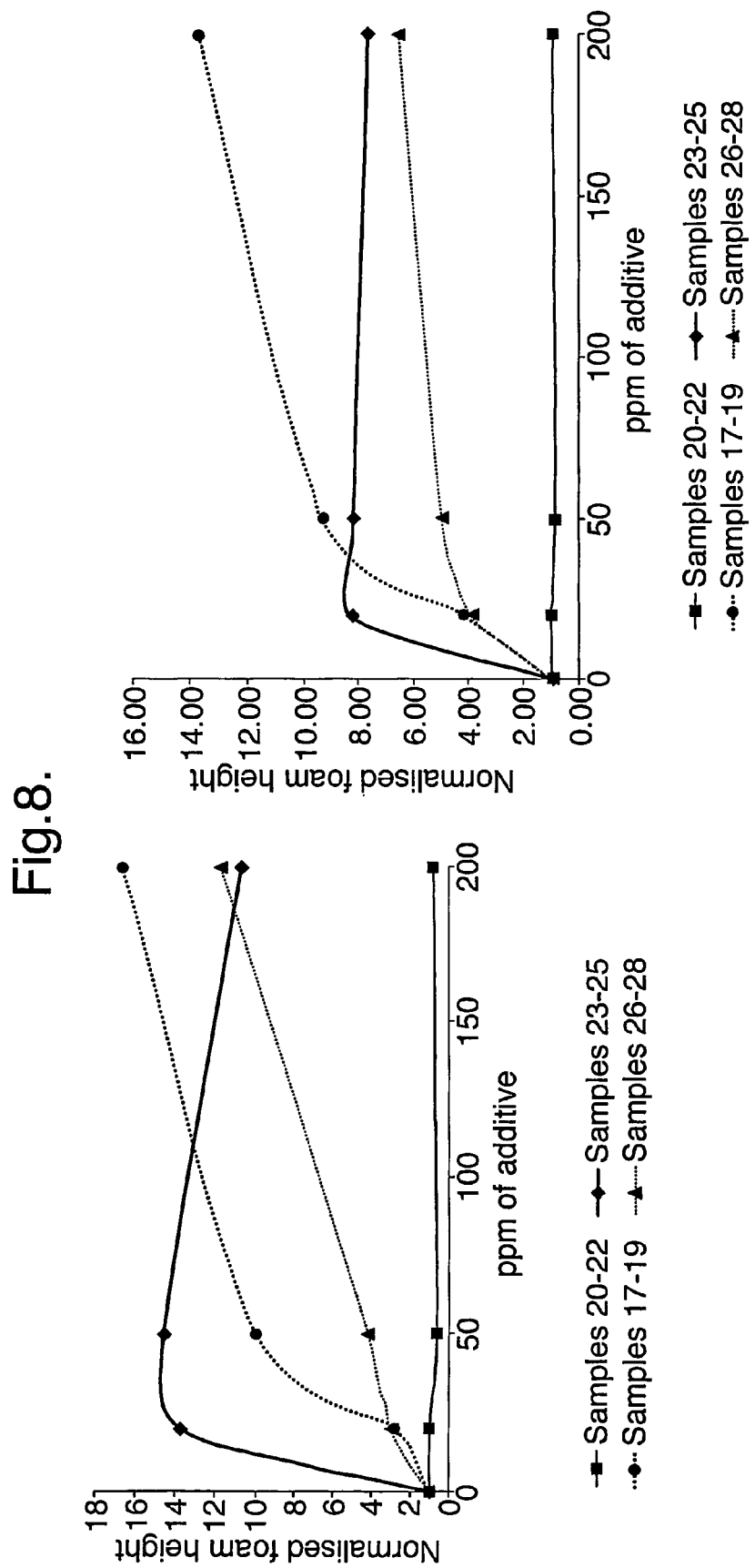
Figure 9:
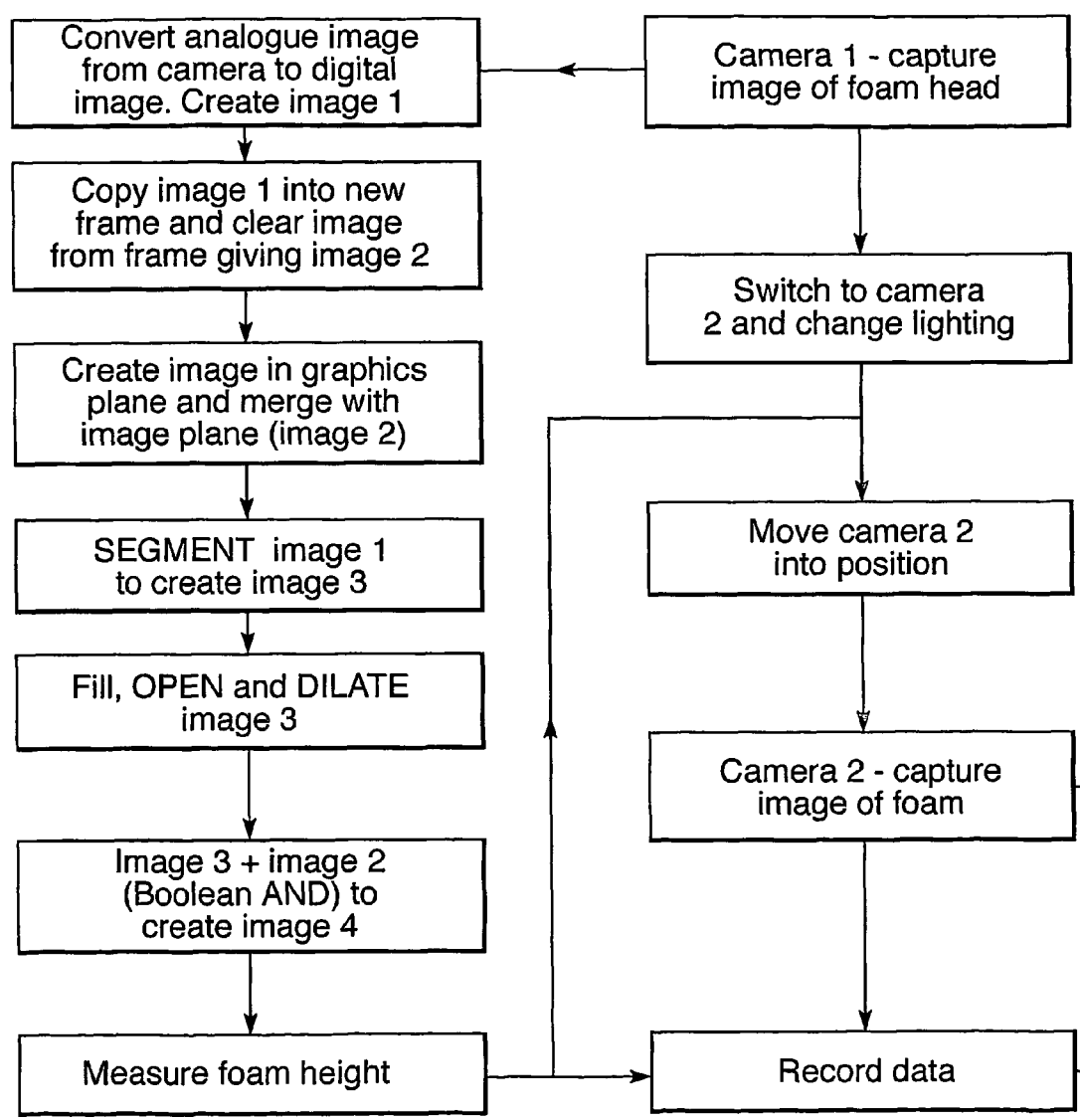
Figure 9:
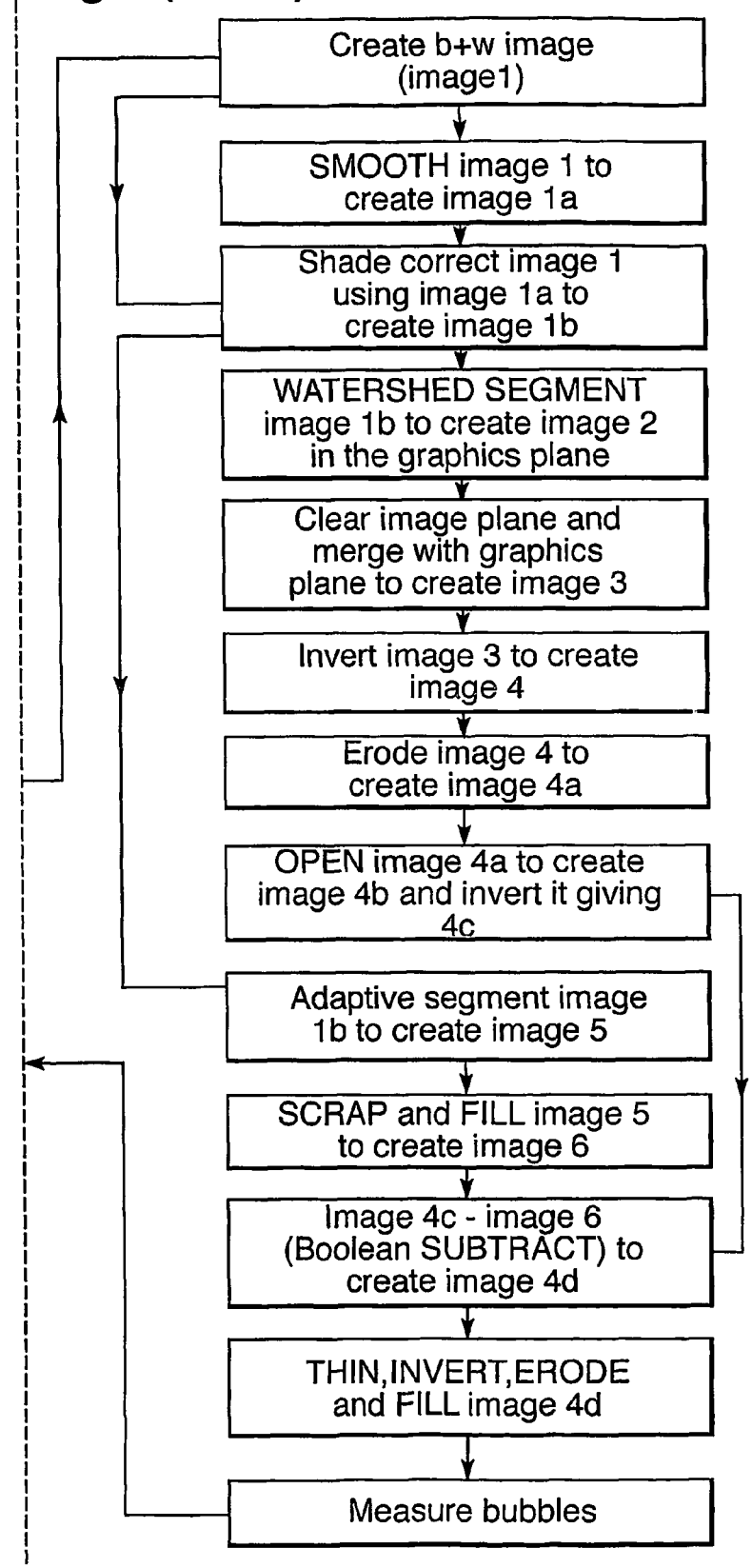

FIG. 5 has two graphs relating to a first set of samples and it is comparing foam height data obtained using an ASTM method (left hand graph) and time to specified height obtained using the invention (right hand graph) and as more particularly described in Example 1;

FIG. 6 has two graphs relating to a second set of samples and it is comparing foam height data obtained using an ASTM method (left hand graph) and time to specified height obtained using the invention (right hand graph) and as more particularly described in Example 1;

FIG. 7 has two graphs relating to a first set of samples and it is comparing foam height data obtained using an ASTM method (left hand graph) and foam height obtained using the invention (right hand graph) and as more particularly described in Example 1;

FIG. 8 has two graphs relating to a second set of samples and it is comparing foam height data obtained using an ASTM method (left hand graph) and foam height obtained using the invention (right hand graph) and as more particularly described in Example 1;

FIG. 9 is a flow diagram of the sequences used to capture images of foam and to process them to obtain information relating to the foam as described in Example 2.

FIG. 10 is a graph of the results of Samples 1 and 3 as described in Example 2 and in Table 9.

Figure 1:
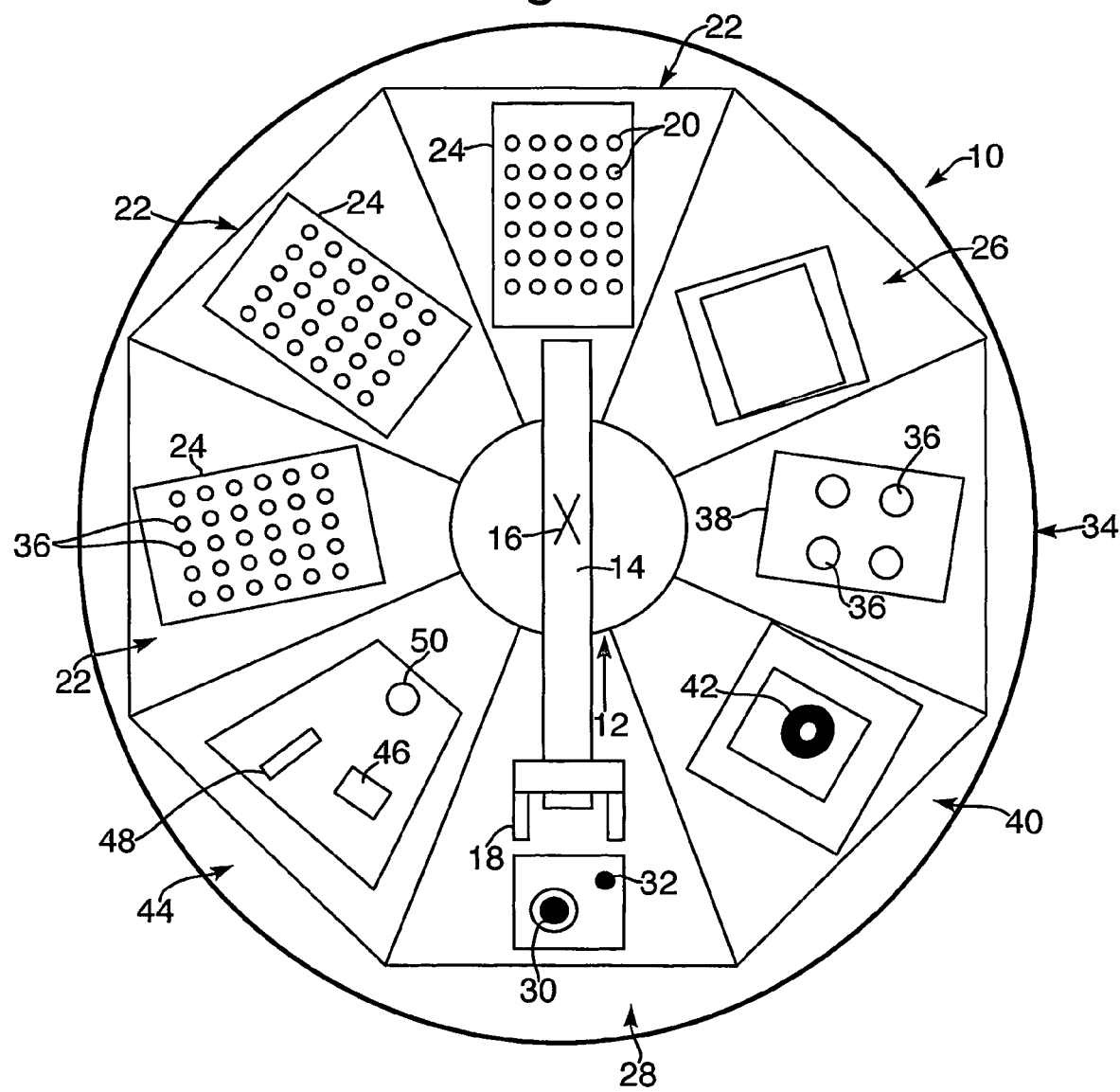
FIG. 1 is a schematic plan view of automated sample handling and measuring apparatus according to the invention.

In FIG. 1, is shown an automatic sample handling and testing apparatus in accordance with the invention. The apparatus 10 has a Zymark XP robot system 12 in which the robot arm 14 is mounted both for rotation about a vertical axis 16 and in the direction of said axis 16. One end of the arm 14 has a gripper mechanism 18 by which sample tubes 20 can be gripped.

Rotation of the robot arm 14 about the axis 16 enables a plurality of workstations to be accessed. The number of workstations in the apparatus 10 can be varied to suit the application. In FIG. 1, the apparatus 10 is shown as having the following workstations:

- three tube holding stations 22 at which racks 24 of sample tubes 20 and cleaning tubes 36 are located;
- a liquid dispensing station 26 at which are located a plurality of liquid dispensers (not shown);
- a gas diffuser parking station 28 having a gas diffuser 30 shown in its parked location, and a location 32 at which a sample tube 20 can be positioned;
- a gas diffuser cleaning station 34 at which are locatable cleaning tubes 36 containing cleaning liquids, the tubes 36 being locatable in an ultrasonic bath 38;
- a foam height measurement station 40 at which is located an opto-electronic device 42 such as a photodiode turbidity detector, available from Zymark Corporation, Zymark Center, Hopkinton, Mass. 01748 USA, which is configured to allow the robot arm 14 to pass the length of a sample tube 20 in front of the detector as the arm 14 moves vertically long the axis 16 and is capable of detecting air/foam and foam/liquid interfaces; and an image capture and analysis station 44 at which are located cameras 46 and 48 and a locator 50 for a sample tube 20.

The cameras 46, 48 were two CCD cameras that were capable of capturing images of foam in the tubes. The camera 46 was an AxioCam MRC camera fitted with a Computar 55 mm f2.8 Telecentric lens set at maximum zoom with a 35 mm extension tube. It is positioned with the front of its lens 1500 mm from the location of the wall of a tube 20. Camera 48 was a Sony XC-75CE fitted with a Pentax 25 mm f1.4 lens located about 280 to 350 mm from the tube 20. Station 44 was surrounded by a non-reflective, light neutral environment to prevent unwanted reflections being captured as parts of the images of the foams. Station 44 was also provided with a cold cathode LP-100 lamp light source positioned above and in front of the tube position relative to the camera 48 so that the foam is lit from the front and at an angle thereto to minimise stray reflections; and a Schott cold light source with a gooseneck fibre optic cable the end of which was located immediately beneath the tube position so that the foam is lit from below when camera 46 was used.

In practise, it is likely only one of the stations 40 and 44 will be present but, for convenience, both are shown. The operation of the stations 40 and 44 is described below in Examples 1 and 2, respectively.

The gas diffuser 30 consists of a metal sinter (10 mm long×10 mm diameter and having 2 micron diameter holes (available from Fisher Scientific, Bishop Meadow Road, Loughborough, Leicestershire LE11 5RG) attached to a length of glass tube 125 mm long×5 mm inside diameter. The glass tube was in turn attached through a flexible air-impervious tube to an Omega Mass Flow Controller having a gas flow range (1-10) ml/min.

In general, the operation of the apparatus 10 is as follows.

A plurality of sample tubes 20 is located in one or more racks at the stations 22 and constituent components of sample liquids to be tested are placed in the liquid dispensers at station 26. Cleaning tubes 36 containing cleaning liquids are located in one rack at one of the stations 22.

The robot arm 14 is rotated about the axis 16 between the stations 22 and 34 to transfer cleaning tubes 36 to station 34. The robot arm 14 is then rotated between the stations 22 and 26 to transfer a sample tube 20 to the station 26 where constituent components of the sample liquids to be tested are added to the sample tube 20 in variably controlled amounts. The robot arm 14 is rotated about the axis 16 to present the sample tube 20 containing the sample to be tested to stations 28 and either 40 or 44 as is described in more detail below in Examples 1 and 2.

Once the sample has been tested, the robot arm 14 returns the sample tube 20 to its location in its rack 22 at the relevant station 22 and then collects the used cleaning tubes 36 and returns them to their rack 24 at the relevant station 22.

The sequence is then repeated, the composition of the samples generated at station 26 to be tested each of differing in its composition to the other samples. The differences between samples may be relatively large when scoping experiments are being performed or may be relatively small when optimisation experiments are being performed.

Reference is now made to the Examples.

EXAMPLE 1

A number of foam assessments were carried out (using the materials identified in Table 1 made up into samples as shown in Table 2).

At one of or more of the stations 22 were located sample receiving glass test tubes 20 (each 125 mm long×25 mm diameter). Samples (15 ml) to be tested were introduced into the tubes 20 from the dispensers at station 26 as described above with reference to FIG. 1. With a sample tube 20 at station 28, the robot 12 introduced into the tube 20 the gas diffuser 30 and then moved the tube 20 with the gas diffuser 30 in it to station 40 at which foam was generated and measured as is described in more detail below.

TABLE 1

Materials tested

| Material No | Material | Description |
|---|---|---|
| M1 | Emkarate* RL 22H Lubricant | A polyol ester refrigerant lubricant available from Uniqema. |
| M2 | Lubricant | A methyl end capped polypropylene glycol. |
| M3 | Zerol 150 | An alkylbenzene available from the Chevron Company. |
| M4 | Tego 793 | An antifoaming agent available from Thomas Goldschmidt. |
| M5 | RC8301 | An antifoaming agent available from Rhein Chemie. |
| M6 | Silicone Fluid 50 | A foam promoting agent available from Akrochem. |
| M7 | Fluorolink D10 | A polydimethyl siloxane foam promoting agent available from Ausimont. |

*Trade mark of the ICI Group of companies.

Following foam generation and measurement, the gas diffuser 30 was removed from the tube 20 and was moved to station 34 at which it was cleaned by being placed in a cleaning tube 36 containing water and air was caused to flow through the diffuser 30, the diffuser 30 then being placed in a cleaning tube 36 containing acetone with the air flow being maintained and then being removed from the acetone and left in air with the air flow being maintained to dry the diffuser 30. During the cleaning phase, the ultrasonic bath 38 was operated. The gas diffuser 30 was then returned to the parking station 28; the sample tube 20 was collected from station 40 and returned to its location in the rack at one of the stations 22; and the cleaning tube 36 containing, water was returned to its rack 24 at the relevant station 22 to be replaced by a fresh tube 36 containing water. In this particular Example, the diffuser 30 is primarily cleaned by the water; the acetone is used primarily as a drying aid. Consequently, it was not necessary to change the cleaning tube 36 containing the acetone between individual tests.

TABLE 2

Samples of Lubricant Compositions

| | Material No | | | | | | |
|---|---|---|---|---|---|---|---|
| 2Sample No | M1 Wt % | M2 Wt % | M3 Wt % | M4 Wt % | M5 Wt % | M6 Wt % | M7 Wt % |
| 1 | 100 | | | | | | |
| 2 | 50 | | | 50 | | | |
| 3 | 50 | 50 | | | | | |
| 4 | 49.99 | 49.99 | | 0.02 | | | |
| | | | | ppm | ppm | ppm | ppm |
| 5 | 50 | 50 | | 20 | | | |
| 6 | 50 | 50 | | 50 | | | |
| 7 | 50 | 50 | | 200 | | | |
| 8 | 50 | 50 | | | 20 | | |
| 9 | 50 | 50 | | | 50 | | |

TABLE 2-continued

Samples of Lubricant Compositions

| 2Sample No | M1 Wt % | M2 Wt % | M3 Wt % | M4 Wt % | M5 Wt % | M6 Wt % | M7 Wt % |
|---|---|---|---|---|---|---|---|
| 10 | 50 | 50 | | 200 | | | |
| 11 | 50 | 50 | | | | 20 | |
| 12 | 50 | 50 | | | | 50 | |
| 13 | 50 | 50 | | | | 200 | |
| 14 | 50 | 50 | | | | | 20 |
| 15 | 50 | 50 | | | | | 50 |
| 16 | 50 | 50 | | | | | 200 |
| 17 | 50 | | 50 | 20 | | | |
| 18 | 50 | | 50 | 50 | | | |
| 19 | 50 | | 50 | 200 | | | |
| 20 | 50 | | 50 | | 20 | | |
| 21 | 50 | | 50 | | 50 | | |
| 22 | 50 | | 50 | | 200 | | |
| 23 | 50 | | 50 | | | 20 | |
| 24 | 50 | | 50 | | | 50 | |
| 25 | 50 | | 50 | | | 200 | |
| 26 | 50 | | 50 | | | | 20 |
| 27 | 50 | | 50 | | | | 50 |
| 28 | 50 | | 50 | | | | 200 |

The specific routine adopted in testing the samples at station 40 was:

1) locate the diffuser 30 in a tube 20 containing the sample for 30 seconds without any airflow during which period the tube 20 is moved to station 40;
2) introduce gas into the sample through the diffuser 30 at a rate of 4 ml/min for 5 minutes unless the foam triggers the optical detector 42 which in turn causes the gas flow to stop and records the time at which the flow is stopped;
3) if, after 5 minutes, the optical detector 42 has not been triggered, stopping the gas flow and causing relative movement between the tube 20 and the detector 42 to enable the detector 42 to determine the relative positions of the air/foam and foam/liquid interfaces to enable the height of the foam to be determined.
4) removing the diffuser 30 from the sample, moving it to station 34 and placing it in a cleaning tube 36 containing water and flowing air through the diffuser for 3 minutes;
5) removing the diffuser 30 from the water and placing it in a cleaning tube 36 containing acetone and flowing air through the diffuser 30 for 0.5 minutes; and
6) removing the diffuser 30 from the acetone and leaving it in air and flowing air through it for 1.5 minutes to dry it.

At this stage, the diffuser is returned to the parking station 28 and is then ready for location in a subsequent sample.

In Table 2, Sample 1 essentially does not foam, Sample 2 is a low foaming composition, Sample 3 is a medium foaming composition and Sample 4 is a high foaming composition.

Sample 3 was used to determine a suitable sample volume to use. This was done by testing portions of different volumes and determining the time taken for the foam to reach the detector 42, which was set at 55 mm above the liquid/air interface. This was done twice. The results are given in Table 3 and are plotted as a graph in FIG. 2. As can be seen from FIG. 2, 15 ml is a suitable sample volume to use to achieve maximum foam height in a reasonable time.

Sample 3 was used to determine a suitable foaming times. This was using the above procedure except the foam height was measured at intervals whilst the gas flow was maintained in the sample. The results are shown in Table 4 and are plotted on a graph in FIG. 3. As can be seen from FIG. 3, the foam height reaches a plateau after about 50-55 seconds and reaches a height of about 8 cm, ie well within the confines of the tube.

TABLE 3

| Volume (ml) | Time (seconds) | Time (seconds) | Average Time (Seconds) |
|---|---|---|---|
| First Run | | | |
| 10 | 147.6 | 153.78 | 150.69 |
| 11 | 61.62 | 64.82 | 63.22 |
| 12 | 58.2 | 56.02 | 57.11 |
| 13 | 53.84 | 53.28 | 53.56 |
| 14 | 52.38 | 49.56 | 50.97 |
| 15 | 47.96 | 46.70 | 47.33 |
| Second Run | | | |
| 10 | 177.84 | 191.02 | 184.43 |
| 11 | 57.74 | 58.02 | 57.88 |
| 12 | 53.28 | 53.50 | 53.39 |
| 13 | 51.26 | 51.78 | 51.52 |
| 14 | 50.34 | 48.30 | 49.32 |
| 15 | 46.74 | 46.70 | 46.72 |

Sample 3 was then used to determine the reproducibility of the technique. This was done by repeatedly testing Sample 3 using a series of tubes 20. The tests were run both forward and reverse in respect of the tube sequence. The weight of the tubes 20 both empty and containing the 15 ml portions of Sample 3 was also recorded. The results of those tests are detailed in Table 5 and are plotted in a graph in FIG. 4. As can be seen from FIG. 3, the test is reproducible within acceptable limits across a series of tubes 20 and is not dependant on sequence direction or on minor variations in tube/sample weight.

Samples using different levels of additives were then tested as described above in this Example. The same Samples were also tested using ASTM D892-95. The results were compared as described below.

To enable a comparison to be made between the ASTM method and the method according to the invention, the results were normalised by setting the results for the Samples containing no additives, ie Samples 2 and 3, as unity (1) and calculating the results of the other Samples as a ratio of the result in question to the result of those Samples 2 and 3. The results obtained are given in Table 6 and are plotted in FIGS. 5 to 8, the ASTM method results being shown in the left hand graph in each of the FIGS. 5 to 8 and the results from the invention being shown in the right hand graph in each of the FIGS. 5 to 8.

TABLE 4

| Run 1 | | Run 2 | | Run 3 | |
|---|---|---|---|---|---|
| Time (seconds) | Height (cm) | Time (seconds) | Height (cm) | Time (seconds) | Height (cm) |
| 30.12 | 5 | 30.1 | 4.2 | 30.1 | 4.3 |
| 31.04 | 4.5 | 31 | 4.8 | 31.02 | 4.8 |
| 32.12 | 4.9 | 32.08 | 4.8 | 32.08 | 5.1 |
| 33.04 | 5.1 | 33 | 5.1 | 33 | 5.4 |
| 34.1 | 5.4 | 34.06 | 5.3 | 34.06 | 5.4 |
| 35.02 | 5.6 | 35.12 | 5.4 | 35.12 | 5.7 |
| 36.08 | 5.7 | 36.04 | 5.6 | 36.04 | 5.8 |
| 37.14 | 6.0 | 37.1 | 5.9 | 37.1 | 6.1 |
| 38.06 | 6.0 | 38 | 6.0 | 38.02 | 6.2 |
| 39.12 | 6.2 | 39.08 | 6.2 | 39.08 | 6.3 |
| 40.04 | 6.5 | 40.14 | 6.4 | 40.14 | 6.6 |
| 41.1 | 6.7 | 41.06 | 6.7 | 41.04 | 6.9 |
| 42.02 | 6.9 | 42.12 | 6.8 | 42.12 | 7 |

TABLE 4-continued

| Run 1 | | Run 2 | | Run 3 | |
|---|---|---|---|---|---|
| Time (seconds) | Height (cm) | Time (seconds) | Height (cm) | Time (seconds) | Height (cm) |
| 43.08 | 7.1 | 43.02 | 7.2 | 43.02 | 7.3 |
| 44 | 7.3 | 44.08 | 7.4 | 44.1 | 7.3 |
| 45.06 | 7.4 | 45 | 7.5 | 45 | 7.6 |
| 46.12 | 7.6 | 46.06 | 7.6 | 46.06 | 7.7 |
| 47.04 | 7.8 | 47.14 | 7.8 | 47.12 | 7.8 |
| 48.1 | 7.8 | 48.04 | 7.8 | 48.04 | 7.8 |
| 49 | 7.8 | 49.1 | 7.9 | 49.1 | 7.9 |
| 50.08 | 7.9 | 50.02 | 7.9 | 50.02 | 7.9 |
| 51 | 7.9 | 51.08 | 7.9 | 51.08 | 8 |
| 52.06 | 8 | 52 | 8 | 52 | 8 |
| 53.12 | 8 | 53.06 | 8 | 53.06 | 8 |
| 54.04 | 8 | 54.12 | 8.1 | 54.12 | 8.1 |
| 55.1 | 8 | 55.04 | 8.1 | 55.04 | 8.1 |
| 56.02 | 8.1 | 56.1 | 8.1 | 56.1 | 8.2 |
| 57.08 | 8.1 | 57.02 | 8.3 | 57 | 8.2 |
| 58 | 8.1 | 58.06 | 8.3 | 58.08 | 9.2 |
| 59.08 | 8.2 | 59.14 | 9.3 | 59.14 | 9.2 |

The data produced in FIGS. 5 and 6 show comparative data between the standard ASTM method and the automated method according to the invention by employing ranking as a function of time taken to produce foam. As higher foaming Samples reach the fixed height in a shorter time as compared to lower foaming Samples, to compare the results with the ASTM foam heights, the results of Samples 2 and 3 were divided by the results of the other Samples to produce the normalised figures.

TABLE 5

| Tube Number | Tube Order −1 −29 | Tube Order −29 −1 |
|---|---|---|
| 1 | 47.20 | 46.34 |
| 2 | 45.78 | 44.88 |
| 3 | 45.78 | 44.16 |
| 4 | 45.74 | 44.90 |
| 5 | 46.48 | 44.92 |
| 6 | 47.90 | 47.06 |
| 7 | 45.04 | 44.92 |
| 8 | 45.04 | 44.90 |
| 9 | 44.32 | 44.18 |
| 10 | 46.48 | 47.06 |
| 11 | 44.30 | 44.92 |
| 12 | 46.50 | 46.34 |
| 13 | 45.76 | 47.06 |
| 14 | 43.60 | 45.64 |
| 15 | 44.32 | 44.90 |
| 16 | 45.04 | 45.64 |
| 17 | 44.32 | 47.08 |
| 18 | 44.24 | 45.62 |
| 19 | 44.30 | 44.90 |
| 20 | 44.30 | 44.88 |
| 21 | 44.22 | 44.92 |
| 22 | 43.58 | 44.90 |
| 23 | 43.58 | 44.90 |
| 24 | 44.34 | 44.92 |
| 25 | 43.58 | 45.62 |
| 26 | 43.58 | 46.36 |
| 27 | 42.88 | 44.18 |
| 28 | 43.60 | 44.18 |
| 29 | 43.58 | 47.06 |
| Average | 44.85 | 45.37 |
| SD | 1.26 | 0.93 |
| RSD | 2.80 | 2.04 |

The ranking compared to the ASTM method is the same but the resolution between samples in not as pronounced. However the time taken to produce the data in accordance with the invention is more rapid than the ASTM method.

Data produced employing the second method of detection, measuring the height of foam produced, shows good comparability to the data produced using the ASTM method on the same sample set. (FIGS. 6 and 7) In this instance, the results for the Samples were divided by the results for Samples 2 and 3 to produce the normalised figures.

The use of a combination of these testing methods allows evaluation of samples with widely differing foaming capabilities without danger of loss of sample containment for high foaming samples without the need to vary the gas flow.

TABLE 6

| Sample No | Time to fixed foam height (s) | Normalised | Height of Foam | Normalised | ASTM Foam Height (mm) | Normalised |
|---|---|---|---|---|---|---|
| 3 | 57.4 | 1.00 | 2.7 | 1.0 | 280 | 1.00 |
| 5 | 51.1 | 1.12 | 5.0 | 1.8 | 420 | 1.50 |
| 6 | 49.9 | 1.15 | 5.5 | 2.0 | 640 | 2.29 |
| 7 | 50.2 | 1.14 | 6.1 | 2.2 | 630 | 2.25 |
| 3 | 57.8 | 1.00 | 3.2 | 1.0 | 280 | 1.00 |
| 8 | 52.2 | 1.11 | 3.8 | 1.2 | 160 | 0.57 |
| 9 | 50.8 | 1.14 | 4.3 | 1.4 | 310 | 1.11 |
| 10 | 51.8 | 1.12 | 4.7 | 1.5 | 320 | 1.14 |
| 3 | 52.7 | 1.00 | 3.3 | 1.0 | 280 | 1.00 |
| 11 | 58.3 | 0.90 | 4.6 | 1.4 | 350 | 1.25 |
| 12 | 55.1 | 0.96 | 4.7 | 1.4 | 375 | 1.34 |
| 13 | 57.3 | 0.92 | 4.7 | 1.4 | 125 | 0.45 |
| 3 | 52.6 | 1.00 | 3.3 | 1.0 | 280 | 1.00 |
| 14 | 50.2 | 1.05 | 5.4 | 1.6 | 304 | 1.09 |
| 15 | 50.2 | 1.05 | 5.5 | 1.6 | 375 | 1.34 |
| 16 | 49.5 | 1.06 | 6.1 | 1.8 | 450 | 1.61 |
| 2 | 172.7 | 1.00 | 0.4 | 1.0 | 30 | 1.00 |
| 17 | 55.1 | 3.13 | 1.6 | 4.1 | 85 | 2.83 |
| 18 | 41.6 | 4.15 | 3.7 | 9.3 | 300 | 10.00 |
| 19 | 39.4 | 4.39 | 5.5 | 13.6 | 500 | 16.67 |
| 2 | 57.4 | 1.00 | 0.7 | 1.0 | 30 | 1.00 |
| 20 | 51.1 | 1.12 | 0.6 | 1.0 | 30 | 1.00 |

TABLE 6-continued

| Sample No | Time to fixed foam height (s) | Normalised | Height of Foam | Normalised | ASTM Foam Height (mm) | Normalised |
|---|---|---|---|---|---|---|
| 21 | 49.9 | 1.15 | 0.5 | 0.8 | 20 | 0.67 |
| 22 | 50.2 | 1.14 | 0.6 | 0.9 | 25 | 0.83 |
| 2 | 300.0 | 1.00 | 0.6 | 1.0 | 30 | 1.00 |
| 23 | 48.0 | 6.25 | 5.0 | 8.2 | 410 | 13.67 |
| 24 | 49.9 | 6.01 | 4.9 | 8.2 | 435 | 14.50 |
| 25 | 53.1 | 5.65 | 4.6 | 7.6 | 320 | 10.67 |
| 2 | 146.5 | 1.00 | 0.7 | 1.0 | 30 | 1.00 |
| 26 | 57.7 | 2.54 | 2.7 | 3.9 | 90 | 3.00 |
| 27 | 47.6 | 3.08 | 3.5 | 4.9 | 125 | 4.17 |
| 28 | 47.1 | 3.11 | 4.6 | 6.5 | 350 | 11.67 |

EXAMPLE 2

Solutions of shampoos were analysed and compared as follows:

At one of or more of the stations 22 were located sample receiving glass test tubes 20 (each 125 mm long×25 mm diameter). Samples (15 ml) to be tested were introduced into the tubes 20 from the dispensers at station 26 as described above with reference to FIG. 1. With a sample tube 20 at station 28, the robot 12 introduced into the tube 20 the gas diffuser 30 and then moved the tube 20 with the gas diffuser 30 in it to station 40 at which foam was generated and measured as is described in more detail below.

Following foam generation and image capture, the gas diffuser 30 was removed from the tube 20 and was moved to station 34 at which it was cleaned by being placed in a cleaning tube 36 containing water and air was caused to flow through the diffuser, the diffuser 30 then being placed in a cleaning tube 36 containing acetone with the air flow being maintained and then being removed from the acetone and left in air with the air flow being maintained to dry the diffuser 30. During the cleaning phase, the ultrasonic bath 38 was operated. The gas diffuser 30 was then returned to the parking station 28 and the sample tube 20 was collected from station 44 and returned to its location in the rack at one of the stations 22. In this particular Example, the diffuser 30 is primarily cleaned by the water; the acetone is used primarily as a drying aid. Consequently, it was not necessary to change the cleaning tube 36 containing the acetone between individual tests.

The test samples were 0.1% by weight of shampoo in deionised water. Foam heights of 3 to 6 cm were generated depending upon the foaming ability of the formulation.

The samples selected were:

Sample 1—Pantene Pro-V shampoo available from The Proctor & Gambel Company

Sample 2—Euro Gold shampoo available from Johnson & Johnson

Sample 3—a development shampoo.

The specific routine adopted in testing the samples was:
1) locate the diffuser 30 in a tube 20 containing the sample for 30 seconds without any airflow during which period the tube 20 is moved to station 44;
2) introduce gas into the sample through the diffuser 30 at a rate of 4 ml/min for 4 minutes;
3) stop the gas flow and capture a first image using the camera 48;
4) analysing the image to generate a foam height measurement and adjusting the relative positions of the tube and the camera 46 such that the camera 46 is located opposite the tube at a position that is halfway between the air/foam and foam/liquid interfaces and capturing a second image of the foam using the camera 46;
5) removing the diffuser 30 from the sample, moving it to station 34 and placing it in a cleaning tube 36 containing water and flowing air through the diffuser for 2 minutes;
6) removing the diffuser 30 from the water and placing it in a cleaning tube 36 containing acetone and flowing air through the diffuser for 0.5 minutes; and
7) removing the diffuser 30 from the acetone and leaving it in air and flowing air through it for 1.5 minutes to dry it.

At this stage, the diffuser 30 is returned to the parking station 28 and is then ready for location in a subsequent sample.

Previous work had established that analysis of bubbles at the water/foam head interface did not lead to strong differentiation of the formulations whereas analysing the bubbles from halfway up the foam head gives better differentiation, ie the foam is "aged" as compared to foam at the water/foam head interface. The images were analysed as described in more detail below.

Similarly as described with reference to Example 1, the conditions (time, flow rates etc) used to generate the foams from the samples were determined before assessing the shampoo samples.

In assessing shampoo samples, it was found that it was necessary prior to running a series of samples to condition the diffuser 30. This is particularly critical if the diffuser 30 has not been used for some time. The conditioning was done conveniently using sodium lauryl ether sulphate (SLES). To condition the diffuser 30, steps 1 to 7 described above were iterated using a number of samples of SLES until the foam heights and the analysed bubble size distribution of the foams were consistent. Once consistency of results had been achieved, actual samples to be tested were then run.

It will be appreciated that, if the samples to be tested contain ingredients significantly different from SLES, then another suitable liquid should be selected to condition the gas diffuser 30.

Analysis of the images was performed using a combination of image processing followed by image analysis. In both cases, a Zeiss KS300 image analyser was employed. The final step of the process is the conversion of the processed image to a binary image where all features (bubbles) are white and the separating bubble walls are black. Image analysis was then a process of measuring parameters associated with the individual white regions in the binary image.

In particular, the image capturing and subsequent processing/analysis was done as follows:

Image Capture

1. Capture image* of whole foam head using the camera 48 and save this image in a designated file and processing and analysing the captured image to provide a measurement for the foam height;
2. switch between cameras 48 and 46 so that the live image comes from the camera 46;
3. turn off the cold cathode LP-100 lamp light source associated with the camera 48 and turn on the Schott cold light source for the camera 46;
4. move the camera 46 and the tube 20 relative to one another to locate the camera 46 at a position opposite the tube 20 that is half the foam height, ie midway between the air/foam and foam/liquid interfaces; and
5. capture an image of bubbles at the glass tube surface using the camera 46 and saving this image in a designated file and processing and analysing the captured image to provide parameters of interest.

*The output from the camera 46 is analogue. The output from the camera 46 is converted into a digital image in a 'framegrabber' board of the computer running the software. It is this digital image that is processed and analysed.

Foam Height Analysis 1. copy the digital image (image 1) generated by the framegrabber board from the output from camera 48 into an electronic frame (image 2) and then clear the frame to create a blank image (new image 2) having the same pixel dimensions as the original digital image (image 1);
2. create a rectangle in a graphics plane associated with the electronic frame and merge the graphics plane with the image plane of image 2. Specify the rectangle is white and the remainder is black thereby creating a binary image (image 2) of a white rectangle, the rectangle having dimensions longer than the anticipated length of the foam being measured and narrower than the width of the internal dimension of the tube and clear the graphics plane of the frame. It is important that the rectangle passes down the central axis of the foam head seen in image 1 but is not as wide as the head;
3. subject the original digital image 1 to a SEGEMENT process to generate a binary image (image 3) and:
   3.1 perform a FILL operation to fill in holes or other defects in the white object (the foam) of image 3;
   3.2 perform an OPEN operation on image 3 to remove the fine structure at the edge of the white object; and
   3.3 perform a DILATE operation on the white object so that it is the same size as the original foam head;
4. subject new image 2 and image 3 to a Boolean "AND" operation to create an image (image 4) representative of the foam height;
5. measure image 4 to determine the foam height. The height is determined by measuring the area and, knowing the width, calculating a mean height measurement over the central part of the foam head; and
6. provide a signal to control the position of the camera 46 and store the height information.

During the above routine, the software loads the calibration file for camera 48 at this magnification so that distances are correct. This calibration step is performed separately through the capture of an image of a standard scale placed in the exact position usually occupied by the glass tube 20.

Foam Bubble Size Measurement

1. Select one information channel, eg red, of the digital image from camera 46 and create therefrom a black and white image (image 1) in an electronic frame;
   1.1. subject image 1 to a smoothing operation using a lowpass filter to create a smoothed image (image 1*a*);
   1.2. subject image 1 to a shade correction process using image 1*a* to produce an image (image 1*b*) corrected for shading differences.
2. subject image 1*b* to a WATERSHED SEGMENTATION process to produce an image (image 2) in a graphics plane associated with the electronic frame, image 2 being a line representation of bubble walls of the foam;
3. clearing image 1 from the image plane of the frame and merging the graphics plane with the image plane of the frame to create an image (image 3) consisting of white lines representing the bubble walls and a black background and clearing image 2 from the graphics plane;
4. inverting image 3 to create an image (image 4) in which the bubbles are white and the bubble walls are now black;
   4.1. on image 4 perform an ERODE operation to remove a line of white pixels from the outside of the white blobs so that the separation between them is greater (image 4*a*);
   4.2. on image 4*a* perform an OPEN operation which removes sharp edges from the white blobs but retains the basic size of the objects and place that image in the same frame as image 4*a* to replace image 4*a* (image 4*b*);
5. subject image 1*b* to a straight ADAPTIVE SEGMENTATION to produce a binary image (the adaptive segmentation is done "locally" in the image not globally) (image 5). The purpose of this step is specifically to produce an binary image of the big bubbles alone to enable features arising from bubbles behind, in the image, the big bubbles to be minimised. This is achieved by setting the size parameter and the threshold parameter (the big bubbles tend to also be lighter) for the adaptive segmentation process before carrying it out. Image 5 essentially contains images of just the big bubbles (or the main parts of them). Image 5 is then subjected to a SCRAP operation to remove small white features and a FILL operation to fill in holes in the white objects so they are more complete to generate an image 6;
6. invert image 4*b* so that is shows white lines and black blobs (image 4*c*). Some of these white lines are incorrect since they are from subsurface bubbles;
7. subject the image 4*c* and image 6 to a Boolean "SUBTRACT" operation to generate an image 4*d*. The Boolean operation causes the white blobs of image 6 cancel out some of the white lines of image 4*c* and those are the lines produced owing to the presence of the subsurface bubbles. Image 4*d* is then subjected to the following operations in sequence;
   7.1. a THIN operation that reduces the width of the lines and a PRUNE operation so that the image 4*d* is now of white lines with no white line "tails" surrounding black blobs;
   7.2. an INVERT operation so that the image 4*d* is of black lines surrounding white blobs;
   7.3. an ERODE operation to obtain better separation between the white blobs;
   7.4. an OPEN operation (ie an ERODE operation followed by a DILATE operation—it tends to erode off sharp edges but leaves the basic size and shape of the object unchanged) giving the finished image 4*d*; and
8. measure the dimensions of the white blobs in image 4*d* and put the data in a database. A calibration carried out at the start of the run is then used for all measured images. This is performed as described earlier by capturing an image of a standard scale placed in the exact position of the tube.

The above-described sequences are set out in FIG. 9 as a flow chart.

It will be appreciated the various electronic operations used to process the images captured by the cameras as described herein, for example watershed and adaptive segmentations, invert, thin, open, erode, dilate etc, are well understood in the art. Information relating to such terms is generally available and, in particular, reference is made to "Computer-assisted microscopy: the measurement and analysis of images", John C. Russ, Plenum Press, New York (1990) and "The Image Processing Handbook" 2nd Edition, John C. Russ, CRC Press, Boca Raton (1995).

The bubble parameters measured were: Area and DCircle (area of the circle with the same area as the object). Data output was done in two ways:

a histogram of counts per DCircle size range (e.g. within 100-150 microns, 150-200)

sum of the areas of the bubbles in each such size range (area is related stereologically to volume)

Important parameters defining the bubble size distribution are seen to be:

1. The range in size between the biggest and smallest bubble.
2. Mean Dcircle.
3. Median DCircle (deviates from the mean if the distribution is skew).
4. Standard deviation in bubble sizes.
5. The amount of skew of the distribution i.e. is the distribution symmetrical or does it have, say, a tail to the high bubble diameter side.

Characteristic images of bubbles were obtained for Samples 1 to 3. High foaming formulations tended to give small bubbles with a narrow size distribution. A summary of the data measured for the Samples is given in Table 7.

TABLE 7

| Foam | Counts | Size range (microns) | Median diameter (microns) | Mean diameter (microns) | Standard Deviation | Skewness |
|---|---|---|---|---|---|---|
| Sample 1 | 1113 | 62-298 | 136.2 | 138.8 | 38.5 | 0.5 |
| Sample 2 | 1433 | 15-380 | 125.8 | 131.8 | 36.6 | 1.5 |
| Sample 3 | 1630 | 15-514 | 135 | 147.7 | 57.8 | 1.9 |

The above data relates to the analysis of just one image from one formulation, though in practice many runs are performed and the data is averaged. It is clear from the above that Sample 3 contains the largest bubbles since the range of bubble diameters is high as is the mean bubble diameter.

Other methods of displaying the data are given below.

For example, the number of bubbles within a certain diameter range may be counted. In Table 8, the skew in the Sample 3 distribution is clear to see since there are a number of counts in the large Dcircle size range.

TABLE 8

| DCIRCLE size range (microns) | | Counts Sample 1 | Counts Sample 2 | Counts Sample 3 |
|---|---|---|---|---|
| 0 | 50 | 0 | 2 | 7 |
| 50 | 100 | 187 | 221 | 213 |
| 100 | 150 | 540 | 864 | 870 |
| 150 | 200 | 298 | 280 | 322 |
| 200 | 250 | 83 | 52 | 119 |

TABLE 8-continued

| DCIRCLE size range (microns) | | Counts Sample 1 | Counts Sample 2 | Counts Sample 3 |
|---|---|---|---|---|
| 250 | 300 | 5 | 10 | 44 |
| 300 | 350 | 0 | 2 | 33 |
| 350 | 400 | 0 | 2 | 17 |
| 400 | 450 | 0 | 0 | 2 |
| 450 | 500 | 0 | 0 | 2 |
| 500 | 550 | 0 | 0 | 1 |
| 550 | 600 | 0 | 0 | 0 |

Another method of displaying the data is given by summing of the areas of the bubbles in each size range (e.g. 100-150 microns etc), see Table 9. This method accentuates the skew in the distribution of Sample 3, the sum of the areas giving a good approximation of the volume distribution of bubbles that exists in the foam. The areas for Samples 1 and 3 are plotted in FIG. 10

TABLE 9

The Sum of the Areas of Bubbles in each Diameter Range

| Max Bubble Diameter (microns) | Sample 1 | Sample 3 |
|---|---|---|
| 50 | 0.00 | 0.00 |
| 100 | 1.29 | 1.10 |
| 150 | 10.89 | 6.92 |
| 200 | 7.46 | 6.77 |
| 250 | 4.64 | 3.04 |
| 300 | 2.56 | 0.29 |
| 350 | 2.70 | 0.00 |
| 400 | 1.81 | 0.00 |
| 450 | 0.29 | 0.00 |
| 500 | 0.35 | 0.00 |
| 550 | 0.21 | 0.00 |
| 600 | 0.00 | 0.00 |

Sum of the areas is in millions of sq microns

The invention claimed is:

1. A method of assessing foam generated from a liquid comprising:
    a) introducing a measured quantity of the liquid into at least one tube;
    b) passing a gas of a predetermined flow rate through the liquid to generate foam;
    c) sensing the presence of foam using an opto-electronic that is positioned proximate the exterior of the at least one tube; and
    d) controlling the flow rate of said passing gas based on a signal from either said sensor or a timer or both.

2. The method of claim 1, wherein the signal is generated upon the sensor detecting the presence of foam.

3. The method of claim 1, wherein the signal is generated from the timer that is set for a predetermined period of time.

4. The method of claim 1, wherein controlling the flow rate of said passing gas includes stopping said flow rate.

5. The method of claim 1, wherein the sensor detecting the presence of the foam generated is proximate the air/foam interface.

6. The method of claim 1, further comprising adjusting the position of either the tube or the sensor, or both, relative to each other, to enable the sensor to sense the presence of foam.

7. The method of claim 6, wherein the adjusted position of the sensor enables detection of the foam proximate either the air/foam or foam/liquid interface.

8. The method of claim 6, wherein the position of the tube is adjusted.

9. The method of claim 6, wherein the position of the sensor is adjusted.

10. The method of claim 1, wherein the sensor is a photo-diode turbidity detector capable of sensing the presence of foam proximate the air/foam interface.

11. The method of claim 1, wherein the sensor is a photo-diode turbidity detector capable of sensing the presence of foam proximate the foam/liquid interface.

12. The method of claim 1, further comprising:
   a) capturing an image of the foam with at least one camera; and
   b) analyzing the captured image for foam quality parameters.

13. The method of claim 12, wherein the at least one camera is a COD camera.

14. The method of claim 1, wherein the at least one tube is two but not more than 100 tubes.

15. The method of claim 1, wherein the method is assessing foam generated from a plurality of liquids, comprising more than 1 but not more than 100 liquids.

16. The method of claim 15, wherein the plurality of liquids are assessed in parallel.

17. The method of claim 16, wherein the plurality of liquids are assessed using a high-throughput screening apparatus comprising a plurality of workstations and a robotic arm having access to the workstations.

18. The method of claim 17, wherein the plurality of workstations comprises:
   i) a first workstation, wherein one or more racks of tubes are located and cleaned;
   ii) a second workstation, wherein a liquid dispensing means is located, comprising a plurality of liquid dispensors;
   iii) a third workstation, wherein cleaning tubes are locatable;
   iv) a fourth workstation, having a parking location for receiving a gas diffuser means can be placed within a liquid such that gas can be passed through the liquid to generate foam, and having a means to control the flow of gas passed through the liquid, and
   v) a fifth workstation, having more than one sensor capable of sensing foam generated from a liquid located in the tube.

19. The method of claim 15, wherein the plurality of liquids are assessed sequentially.

* * * * *